United States Patent [19]

Chang et al.

[11] Patent Number: 5,196,096
[45] Date of Patent: Mar. 23, 1993

[54] METHOD FOR ANALYZING THE ADDITION AGENTS IN SOLUTIONS FOR ELECTROPLATING OF PBSN ALLOYS

[75] Inventors: I-Chia H. Chang, Peekskill; Wilma J. Horkans, Ossining, both of N.Y.

[73] Assignee: International Business Machines Corporation, Armonk, N.Y.

[21] Appl. No.: 857,024

[22] Filed: Mar. 24, 1992

[51] Int. Cl.$^5$ .......................................... G01N 27/26
[52] U.S. Cl. .................................. 204/153.1; 204/413; 204/405; 204/434
[58] Field of Search ...................... 204/153.1, 434, 413, 204/405, 153.23

[56] References Cited

U.S. PATENT DOCUMENTS

| | | | |
|---|---|---|---|
| 3,808,116 | 4/1974 | Webb | 204/413 |
| 3,838,032 | 9/1974 | Yarnilsky | 204/412 |
| 4,142,944 | 3/1979 | Smith | 204/413 |
| 4,182,638 | 1/1980 | Cooke | 204/413 |
| 4,220,515 | 9/1980 | deKreuk | 204/413 |
| 4,631,116 | 12/1986 | Ludwig | 204/434 |

OTHER PUBLICATIONS

"The Polarographic Analysis Of Tin And Tin Alloy Plating Solutions" by A. E. Knotowicz, et al., published by The Patent Button Company, Waterbury, Conn., (1989), pp. 602–606.

"Cyclic Voltammetric Stripping Analysis of Acid Copper Sulfate Plating Baths", by Ronald Haak, et al., (Apr. 1981) pp. 52–55.

"Cyclic Voltammetric Stripping Analysis Of Acid Copper Sulfate Plating Baths", by Ronald Haak, et al., (Mar. 1982) pp. 62–66.

"Determination Of The Individual Additive Components In Acid Copper Plating Baths" by Walter O. Freitag, et al., (Oct. 1983) pp. 55–60.

"Model 384B Polarographic Analyzer Instruction Manual" Published by Princeton Applied Research Corporation, Copyright 1983, 87, 88, pp. V-24–V-28.

"Monitoring Acid Copper Plating Baths", by S. Shawn Heberling et al., PC FAB, Aug. 1989, pp. 72–84.

"Electroplated Solder Joints For Flip-Chip Applications" by Edward K. Yung, IEEE Transactions On Components, Hybrids, And Manufacturing Technology, vol. 14, No. 3, Sep., 1991, pp. 549–559.

*Primary Examiner*—John Niebling
*Assistant Examiner*—Bruce F. Bell
*Attorney, Agent, or Firm*—Sterne, Kessler, Goldstein & Fox

[57] ABSTRACT

A method for measuring concentrations of addition agents in solutions of additive mixtures, namely for monitoring additives in PbSn plating solutions, comprising the steps of: (a) preparing a basis solution which contains an electroactive species whose electroreduction reaction is sensitive to the additive of interest; (b) preparing calibration standard sample solutions comprising appropriate concentrations of all species other than the additive; (c) preparing the working solution whose additive concentration is to be determined; (d) applying a pulse voltammetry technique, at a hanging Hg drop electrode, to a sample of the basis solution located in a cell of a polarographic analyzer; (e) thereafter measuring the polarographic peak height for the indicator reaction in the basis solution; (f) adding a measured amount of the working solution to the basis solution sample in the cell; (g) thereafter measuring the peak height for the indicator reaction in the mixed solution of step (f); and (h) repeating steps (f) and (g) until the peak height has dropped to a constant value.

6 Claims, 2 Drawing Sheets

METHOD FOR ANALYZING THE ADDITION AGENTS IN SOLUTIONS FOR ELECTROPLATING OF PBSN ALLOYS

TECHNICAL FIELD

The present invention relates generally to the field of electroplating. More particularly, the invention relates to the analysis of addition agents in electroplating solutions. Still more particularly, the invention describes a polarographic technique for reliably analyzing addition agents in methane sulfonic acid solutions for the electroplating of PbSn alloys.

BACKGROUND ART

Successful electroplating of some metals and alloys depends critically on the control of species other than the metal cations in the plating solution Among these species are the "additives" or "addition agents" that must be included to give the necessary properties of the deposited material. The addition agents are notoriously difficult to control. A primary difficulty is that they are often purchased from outside vendors, and therefore the identities of the addition agents are often not known. Even for known compounds, good techniques may not exist for analysis in the matrix of the plating solution. Additionally, the additives are usually mixtures of different kinds of chemicals and may be present at very low concentrations.

The copper system demonstrates the current state of the art of additive analysis. Copper deposition from acid $CuSO_4$ is a relatively old technology. There have been years of work on the analysis of the additives in the Cu plating solution. The monitoring methods are semi-quantitative, at best. The amount of Cu plated in cyclic voltammetry, taken to be measurable from the stripping charge, was shown to give some measure of the additive levels in the solution. See, for example, R. Haak, C. Ogden, and D. Tench, Plating, 64(4), 52 (Apr 1981); R. Haak, C. Ogden, and D. Tench, *Plating*, 65(3), 62 (Mar. 1982). This CV method is not an analytical procedure as the term is generally understood: it is not specific for a given chemical compound, and the relationship between measured charge and solution concentration is not direct. In addition, the CV measures the aggregate effects of all of the additive components. Some effort has been made to use the technique to determine the individual components of a multi-component additive (see W. O. Freitag, C. Ogden, D. Tench, and J. White, *Plating*, 70(10), 55 (Oct. 1983)), but it is questionable whether such a procedure can be the basis of plating solution control.

A quantitative analytical technique, liquid chromatography, is available for some of the components of some electroplating solutions (see S. S. Heberling, D. Campbell, and S. Carson, *PC Fab*, Aug. 1989, p. 72). One of the more useful examples is the HPLC analysis of the MD (or Carrier) component of the SelRex Cubath M-Hy acid copper plating solution. Even in this particular plating solution, however, some of the additive components cannot be separated or detected with HPLC. The chromatographic analysis thus allows only partial control of the plating process.

The present inventors have developed a method, disclosed in U.S. patent application Ser. No. 07/701,278, filed May 16, 1991, the entire disclosure of which is incorporated herein by reference thereto, that allows the separate determinations of the MD (Carrier) and M-Lo (Leveller/Ductilizer) components of SelRex Cubath M-Hy. An improved cyclic voltammetric method can be used to determine M-Lo only. The combination of HPLC and CV can thus be used to monitor and control both of the components of the acid-copper additives. The common CV technique measures the amount of Cu deposited as a function of the addition of known volumes of an unknown solution to an additive-free "basis solution." A calibration with a solution of known concentration allows the calculation of the additive concentration in the unknown. The modification that allows CV to be sensitive only to one component of the additive (in this case, M-Lo) is the incorporation in the basis solution of all of the other solution components, including the other additive components (in this case, MD).

The example of Cu shows the formidable problems presented in monitoring and control of plating solutions. The Cu system is, however, much better understood than some other systems of practical interest. The present invention addresses the issue of control of PbSn plating systems. These alloys also require the use of appropriate additives in order to obtain the necessary deposit properties.

The technology of PbSn plating is presently evolving to a system of novel chemistry—solutions based on methane sulfonic acid. PbSn electroplating techniques generally are described in E. K. Yung, and I. Turlik, "Electroplated Solder Joints for Flip-Chip Applications," IEEE Trans. on Components, Hybrids, and Manufacturing Technology, Vol. 14, No. 3, Sept. 1991, the disclosure of which is incorporated herein by reference. The MSA-based PbSn plating solutions give good alloy deposits and eliminate some of the environmental and health hazards associated with the commonly used fluoroborate-based solutions. Since they have been only recently introduced, however, they have not been as extensively studied. Monitoring techniques have not been extensively developed. The vendors supply specifications for analytic procedures for all of the solution components. The present inventors have found these procedures to be unacceptable for the monitoring of the additive system in the solution being used, namely, the LeaRonal Solderon SC solution. The present invention describes a new, better technique for determining the SC levels in PbSn plating solutions.

The present invention overcomes the deficiencies and problems associated with the conventional monitoring technology.

DISCLOSURE OF INVENTION

This invention comprises a method for measuring concentrations of addition agents in solutions of additive mixtures, namely for monitoring additives in PbSn plating solutions. The method comprises the steps of:
(a) preparing a basis solution which contains an electroactive species whose electroreduction reaction is sensitive to the additive of interest and which can be used as an indicator reaction for the determination of the additive concentration;
(b) preparing calibration standard sample solutions comprising appropriate concentrations of all species other than the additive in the vicinity of their expected concentrations in the working solution at a series of appropriately chosen concentrations;
(c) sampling the working solution whose additive concentration is to be determined;

(d) applying a pulse voltammetry technique, preferably square wave voltammetry, at a hanging Hg drop electrode in a sample of the basis solution;

(e) thereafter measuring the polarographic peak height for the indicator reaction in the basis solution (the differential current for the reduction of the indicator species);

(f) adding a measured amount of the additive-containing solution to the basis solution sample in the cell;

(g) thereafter measuring the peak height for the indicator reaction in the mixed solution of step (f);

(h) repeating steps (f) and (h) until the peak height has dropped to a constant value;

(i) plotting a peak height for the indicator reaction in the mixed solution against the corrected volume addition (the total volume of the additions divided by the sum of the added volumes and the original volume) of the solution;

(j) determining the endpoint volume percent necessary to cause 50% of the overall change in peak height;

(k) plotting a calibration curve by
  (1) determining the endpoint for a given number of calibration concentrations, and
  (2) plotting the concentrations of the standards against the reciprocal of the volume percent addition necessary to the endpoint, (l) repeating steps (f) through (j) for the unknown working solution; and (m) determining the concentration of the unknown either from the slope of the calibration curve or by directly reading the concentration at the appropriate reciprocal endpoint volume.

The foregoing and other objects, features and advantages of the invention will be apparent from the following more particular description of the preferred embodiment of the invention, as illustrated in the accompanying drawings.

BEST MODE FOR CARRYING OUT THE INVENTION

Figure 1:
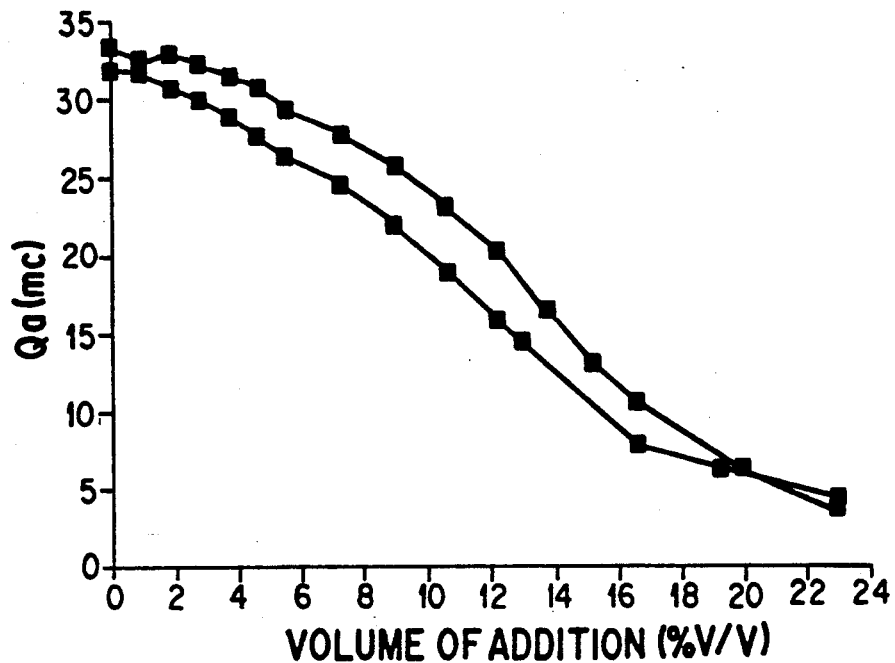
FIG. 1 shows a CV measurement of SC additive, using a Pt rotating disk electrode (RDE)

This invention comprises the use of polarographic techniques for the quantitative analysis of additives in PbSn plating solutions. These techniques are relatively simple, reliable and reproducible, unlike the previously described techniques. The method will be illustrated for the SC Additive in LeaRonal SolderOn PbSn plating solutions (as modified for the plating of high-Pb alloys). Polarographic techniques have also been developed for $Pb^{2+}$ and $Sn^{2+}$ analyses. Thus, all of the critical components of the PbSn plating solutions can be determined by polarography.

There are two additive systems for SolderOn plating solutions, called PC and SC.

The PC addition agent is supplied as two components: the Carrier and the Additive The published analytical procedure for the PC Additive is solvent extraction and spectrophotometric determination. The recommended PC Carrier method is cyclic voltammetry. The LeaRonal CV procedure has been studied in considerable detail by the present inventors. It has not proven useful for analysis of the additive.

Addition agents can be monitored electrochemically because they influence the kinetics and mechanism of the electroreduction of the metal ions to form the deposit. Although the CV methods used for additives in Cu or PbSn plating are procedurally similar, the utility of CV as a monitor is very different in these two systems. In either case, a solution is placed in the electrochemical cell that contains all of the components of the plating solution except the additive. A rotating disk working electrode is used, and thus the mass transport conditions are carefully controlled. The electrode potential is cycled, repeatedly plating the metal or alloy in the cathodic sweep and stripping it in the anodic sweep. As additions of the additive-containing solution (either the unknown solution or a calibrating solution) are made to the cell, the charge consumed in the metal plating is measured as a function of the volume of the addition.

The charge added volume curve for the PC additive for PbSn has a sigmoid shape: there is a nearly constant plating charge with the initial additions of the additive-containing solution, and then the charge drops rapidly to a low value after a critical addition. On solid electrodes, repeated measurements were found to be extremely irreproducible. Even the charge in additive-free solutions could not be reproduced, despite rigorous cleaning of the electrodes. The end-point at which the charge dropped from its initial to its final value varied wildly. The measurement-to-measurement variation for a given PC Carrier concentration was as great as that for PC Carrier concentrations differing by a factor of 2. This procedure thus does not even give reliable qualitative information about the additive levels in the PbSn plating solutions.

The situation for SC addition agent is similar. This additive is supplied as a single solution. The published analytical procedure is an absorbance measurement after solvent extraction. This procedure has been found to be difficult and unreliable A CV technique has been suggested as an alternative.

The CV procedure for SC on solid electrodes is, however, unsuitable as an analytical method. It suffers from the same irreproducibility observed in all the PbSn systems examined. Additionally, the behavior is different from the PC system in that the CV procedure has no clear end-point. FIG. 1 shows a CV measurement of SC additive, using a Pt rotating disk electrode (RDE). The basis solution was 300 ml/l SolderOn Lead Concentrate, 70 ml/l SolderOn Acid Concentrate. The amount of Pb plated, determined from the stripping charge via cyclic voltammetry, is plotted in FIG. 1 against the volume of additions of a solution containing 300 ml/l Lead Concentrate, 30 ml/l Tin Concentrate, 70 ml/l Acid Concentrate, and 100 ml/l SC Additive. The two curves represent two measurements under the same conditions. There is a considerable error in each point, since the charge does not reach a steady value in repeated cycling. There is a large variation between the two measurements. Finally, there is no clear end-point that can be related to the SC concentration.

All of these problems are eliminated by the use of Hg electrodes and polarography. The polarographic technique employed is square wave voltammetry (SWV). This technique uses a single hanging Hg drop for the entire sweep. It thus produces a rapid measurement compared to conventional polarography. While SWV polarography is preferred for this invention, it should be understood that other types of polarography and pulse voltammetry techniques on a Hg electrode are applicable to the method of this invention.

A stock solution was prepared consisting of 300 ml/l Lead Concentrate and 70 ml/l Acid Concentrate For the polargraphic measurements, the stock solution was diluted by a factor of 100 with 0.1M methane sulfonic acid (MSA) to prepare the basis solution. The unknown and calibrating solutions were also diluted 100X with MSA, so that the overall metal concentration remained nearly constant during the addition of these solutions to the basis solution during the measurement.

Following is a sample square wave voltammetry (SWV) procedure for the determination of solution components.

A. Preparation of Solutions

1. Preparation of Basis Solutions.
   a. Prepare a concentrated basis solution. In the preferred example, the concentrated basis solution is composed of 30 v/v (volume percent) SolderOn Lead Concentrate +7 v/v SolderOn Acid Concentrate. This yields a final acid concentration of 67.5 mM $Pb^{2+}$ and 0.5N methane sulfonic acid.
   b. Dilute the concentrated basis solution 1:100 by volume with 0.1N methane sulfonic acid.
2. Preparation of Standard Solutions.
   a. Prepare a series of concentrated standard sample solutions. The standards should approximate the total expected metal content of the unknowns (that is, the working plating solutions). In addition, the standard solutions contain the addition agent at known concentrations. In the preferred example, the standard solutions consist of 30 v/v SolderOn Lead Concentrate +7 v/v SolderOn Acid Concentrate +X v/v SolderOn SC Concentrate, where X is generally 5.0, 7.5, and 10.0 v/v.
   b. Dilute each of the above concentrated standard solutions 1:100 with 0.1N methane sulfonic acid.
3. Preparation of Unknown solution.
   a. Sample the working plating solution.
   b. Dilute the sampled working solution 1:100 with 0.1N methane sulfonic acid.

B. Analysis of Unknown

1. Pipette a known amount of the dilute basis solution into the cell of the polarographic analyzer. In the preferred example, a 10 ml volume is used.
2. Choose the conditions of the polarographic analysis. In the preferred example, the potential is swept from −0.1 V to −0.8 V vs. Ag/AgCl at the instrumental defaults for square wave voltammetry (a scan increment of 2 mV, pulse height of 20 mV, and frequency of 100 Hz). Using square wave voltammetry (SWV) at a hanging Hg drop electrode, determine the peak height for $Pb^{2+}$ reduction (i.e., for the formation of the Pb amalgam).
3. Add a small volume of either the diluted standard solution (for calibration) or of the unknown (for analysis). A volume of 0.5 ml was used in the preferred example.
4. Remeasure the $Pb^{2+}$ peak height in SWV.
5. Repeat steps B. 3 and B. 4 until the peak height has dropped to a constant value.
6. Plot the SWV peak height against the corrected volume addition (the total volume of the additions divided by the sum of the added volume and the original volume) of the solution (either the calibrating or the unknown solution).
7. Determine the endpoint volume, the volume percent addition at which the drop in peak height from its initial value is 50% of the total drop in peak height achieved when a constant final value is reached.
8. Plot a calibration curve.
   a. Determine the endpoint volume for an appropriate number of calibration concentrations.
   b. Plot the concentration of the standard against the reciprocal of the endpoint volume.
9. Using the endpoint volume for the unknown, determine its concentration from the calibration curve, either by reading the concentration directly from the curve at the appropriate reciprocal endpoint volume or by using the slope of the calibration curve.

Figure 2:
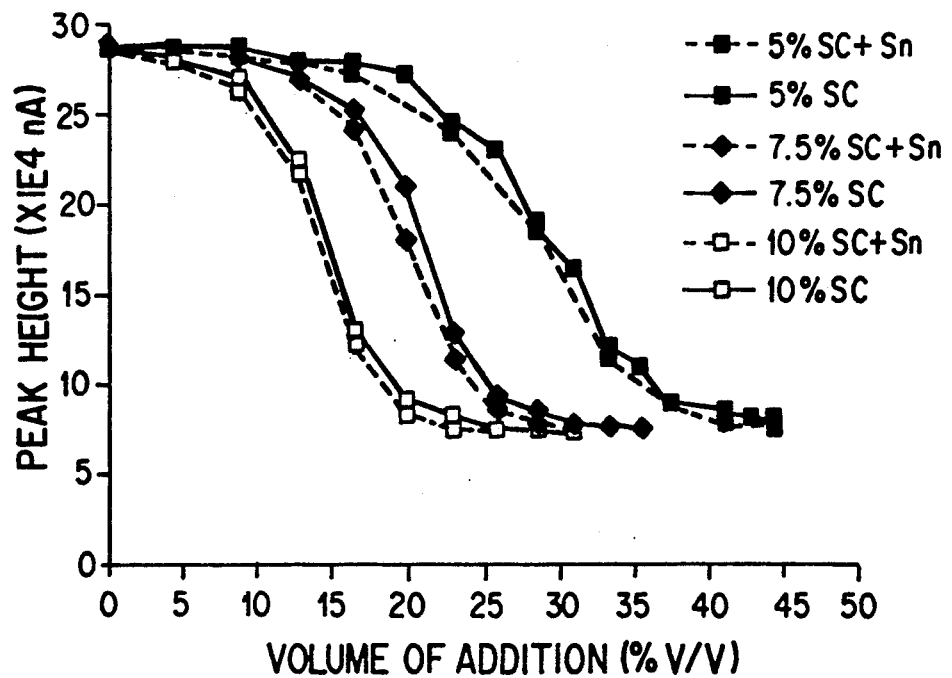
FIG. 2 shows typical results using the procedure of this invention.

FIG. 2 shows typical results using the above-described procedure. The solutions examined all had original concentrations before dilution of 300 ml/l Lead Concentrate, 70 ml/l Acid Concentrate, either 0 or 30 ml/l Tin Concentrate, and 50, 75, or 100 ml/l SC Additive. Such solutions plate high-PbSn alloys. Since $Pb^{2+}$ is the preponderant cation in these solutions, a $Pb^{2+}$ basis solution with no $Sn^{2+}$ gives excellent results. FIG. 2 shows that there is no appreciable difference in measurements of $Sn^{2+}$-free solutions an those containing $Sn^{2+}$. There is excellent reproducibility of each measurement.

Figure 3:
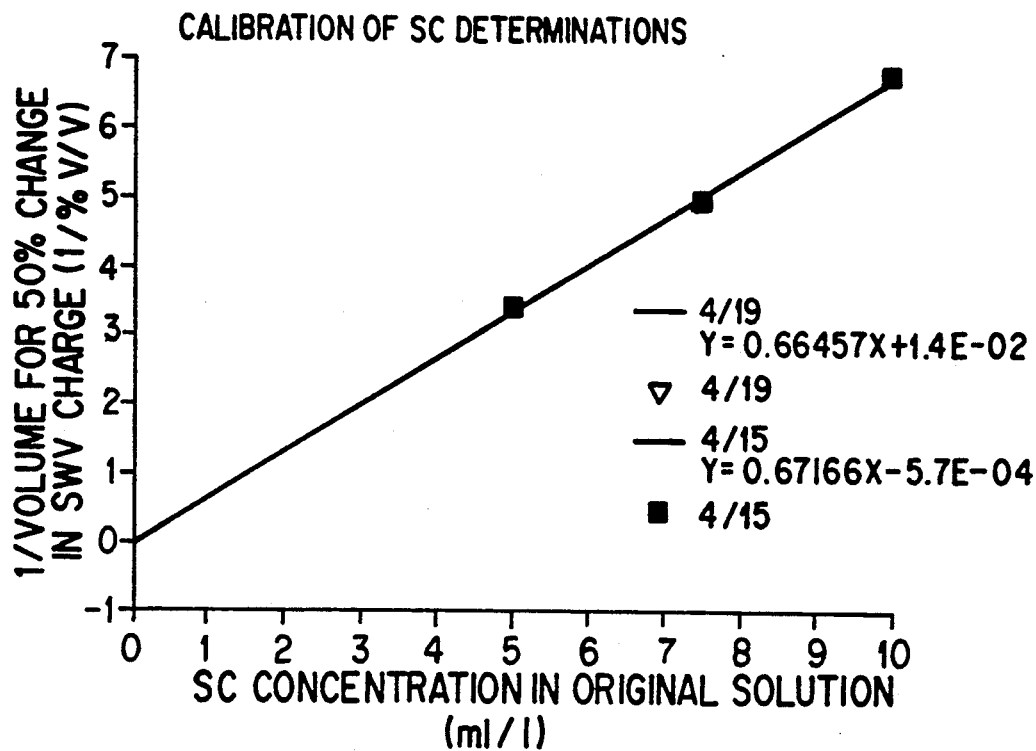
FIG. 3 shows a calibration curve of SC determinations and demonstrates the reproducibility of the method of this invention.

The end-point is taken as the corrected volume addition that produces half of the overall change in polarographic peak height. The calibration curve, FIG. 3, is produced by plotting the reciprocal of this volume against the SC concentration. FIG. 3 represents two sets of measurements and demonstrates the reproducibility of the method.

Figure 4:
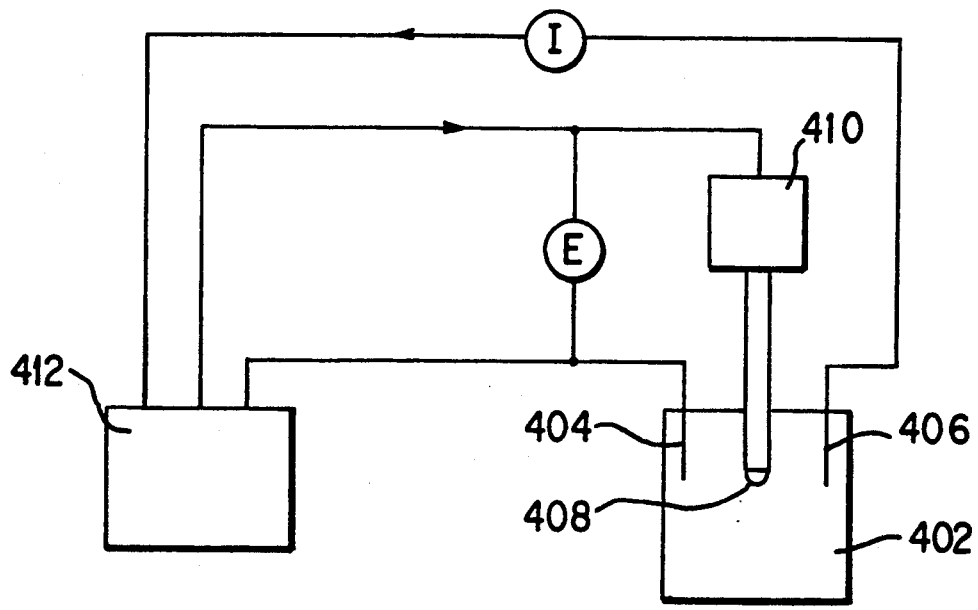
FIG. 4 shows a block diagram form of an apparatus used to conduct the method of this invention.

A typical setup of the type used with the above-described procedures is shown in FIG. 4. A sample cell 402 contains a reference electrode 404, a counter electrode 406, and a hanging Hg drop electrode (HMDE) 408. The HMDE is controlled by an HMDE controller 410. The reference electrode 404, counter electrode 406, and HMDE controller 410 are connected to a standard polarographic analyzer 412. In the presently preferred embodiment, the analyzer 412 is a Model 384B Polarographic Analyzer, manufactured by Princeton Applied Research Corporation. The controller 412 may be an EG&G PARC Model 303A SMDE (Static Mercury Drop Electrode).

The potential drop E between the reference electrode 404 and the hanging Hg drop electrode 408 is controlled by the analyzer 412 and determines the flow of current I through Solder Joints for Flip-Chip Applications," IEEE Trans. on the Hg drop 408, the solution, and the counter electrode 406.

The procedure of the invention has been demonstrated in routine SC analyses of PbSn plating solutions. There was no available method prior to this. It is anticipated that this or a similar modified technique is extendable to the PC additive. It should eliminate the irreproducibility inherent in the CV measurements on solid electrodes.

Modification of the basis solution composition may be necessary in the analysis of solutions for plating higher-Sn alloys. The simplicity of the all-$Pb^{2+}$ basis solution may be lost if the plating solution contains major amounts of $Sn^{2+}$. It is possible, in principle, to include $Sn^{2+}$ in the basis solution. In this case, it will be necessary to protect the Sn(II) against oxidation to Sn(IV). The antioxidant catechol achieved this goal without interfering with the SWV analyses of $Pb^{2+}$ and $Sn^{2+}$. Thus, modifications of the technique for a variety of plating solutions should not be difficult.

While the invention has been particularly shown and described with reference to a preferred embodiment thereof, it will be understood by those skilled in the art that serious changes to the foregoing in form and details may be made therein without departing from the spirit and scope of the invention.

Having thus described our invention, what we claim as new and desire to secure by Letters Patent is:

1. A method for measuring concentrations of addition agents in solutions of additive mixtures, comprising the steps of:
    (a) preparing a basis solution which contains an electroactive species whose electroreduction reaction is sensitive to the additive of interest;
    (b) preparing calibration standard solutions comprising appropriate concentrations of all species, other than the additive of interest, in the vicinity of their expected concentrations in the working solution at an appropriately chosen series of concentrations;
    (c) sampling a working solution whose additive concentration is to be determined;
    (d) applying a pulse voltammetry technique at a hanging Hg drop electrode to a sample of said basis solution;
    (e) thereafter measuring the polarographic peak height for the indicator reaction in said basis solution;
    (f) adding a measured amount of one of said additive-containing sample solutions to said basis solution sample in said cell;
    (g) thereafter measuring the peak height for said indicator reaction in the mixed solution of step (f); and
    (h) repeating steps (f) and (g) until said peak height has dropped to a constant value.

2. A method according to claim 1, wherein steps (f)-(h) comprise the further steps of:
    (i) adding a measured amount of a first one of said standard sample solutions to a first sample of said basis solution in said cell;
    (j) thereafter measuring the peak height for said indicator reaction in the mixed solution of step (i);
    (k) repeating steps (i) and (j) until said peak height has dropped to a constant value; and
    (l) thereafter repeating steps (i) through (k) for each other standard sample solution.

3. The method according to claim 2, comprising the further steps of:
    (m) plotting a peak height for said indicator reaction in the mixed solution of steps (i) through (1) against the corrected volume addition (the total volume of the additions divided by the sum of the added volumes and the original volume) of the solution;
    (n) determining the endpoint volume percent necessary to cause 50% of the overall change in peak height;
    (o) plotting a calibration curve by
        (1) determining the endpoint for a given number of calibration concentrations, and
        (2) plotting the concentration of said standards against the reciprocal of the volume percent addition to said endpoint; and
    (p) determining the concentration of the unknown from the calibration curve.

4. The method according to claim 1, wherein said pulse voltammetry technique comprises square wave voltammetry.

5. The method according to claim 1, wherein said unknown working solution comprises a PbSn plating solution.

6. The method according to claim 1, wherein step (a) further comprises the steps of:
    (i) mixing a lead concentrate and an acid concentrate; and
    (j) adding methane sulfonic acid to the lead-acid mixture in an amount sufficient to dilute the lead-acid mixture by a factor of approximately 100.

* * * * *